(12) United States Patent
Duriez et al.

(10) Patent No.: US 7,008,793 B2
(45) Date of Patent: Mar. 7, 2006

(54) METHOD AND DEVICE FOR TAKING A SAMPLE OF AN EMULSION CIRCULATING IN A LINE

(75) Inventors: Gilbert Duriez, Rueil-Malmaison (FR); Aurélie Mouret, Houilles (FR); Christine Noïk, Le Pecq (FR); Gérard Papon, Les Essarts-le-Roi (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 629 days.

(21) Appl. No.: 09/971,586

(22) Filed: Oct. 9, 2001

(65) Prior Publication Data

US 2002/0041832 A1 Apr. 11, 2002

(30) Foreign Application Priority Data

Oct. 9, 2000 (FR) .................................. 00 12961

(51) Int. Cl.
 *G01N 33/24* (2006.01)
(52) U.S. Cl. ............................ 436/29; 436/28; 436/30; 436/31; 73/61.41; 73/61.44; 73/64.56; 73/152.11; 73/152.23; 73/863.71
(58) Field of Classification Search ............ 436/28–31; 422/62; 73/61.41, 61.44, 64.56, 152.11, 73/152.23, 863.71
See application file for complete search history.

(56) References Cited

U.S. PATENT DOCUMENTS

| 1,837,858 | A | | 12/1931 | Grace |
| 3,083,577 | A | * | 4/1963 | Moore et al. ............. 73/863.71 |
| 3,084,555 | A | | 4/1963 | Perilloux |
| 4,167,117 | A | * | 9/1979 | Stokley et al. ........... 73/863.58 |
| 5,251,488 | A | * | 10/1993 | Haberman et al. ........ 73/861.04 |
| 5,333,496 | A | * | 8/1994 | Fenelon ........................ 73/202 |
| 5,460,054 | A | * | 10/1995 | Tran ......................... 73/863.61 |
| 6,182,505 | B1 | * | 2/2001 | Segeral ....................... 73/61.44 |

FOREIGN PATENT DOCUMENTS

| FR | 2590185 | 5/1987 |
| WO | 9900656 | 1/1999 |

* cited by examiner

*Primary Examiner*—Jill Warden
*Assistant Examiner*—LaToya Cross
(74) *Attorney, Agent, or Firm*—Antonelli, Terry, Stout and Kraus, LLP.

(57) ABSTRACT

The present invention is intended to take a sample of an emulsion circulating in a line. The emulsion is momentarily diverted from the main circulation line 1 thereof to a bypass line 2. By restoring circulation of the emulsion in main line 1, an emulsion sample still present in bypass line 2 is confined under pressure. The emulsion sample is then stabilized according to a well-known method. Since the size and the distribution of the drops no longer evolve with time, the sample can be observed and analyzed after sampling. The invention more particularly applies to the field of petroleum industry and it is notably intended to take a sample of a petroleum effluent in form of an emulsion at wellheads.

9 Claims, 1 Drawing Sheet

METHOD AND DEVICE FOR TAKING A SAMPLE OF AN EMULSION CIRCULATING IN A LINE

FIELD OF THE INVENTION

The present invention relates to a method for taking a sample, with a view to analysis, of an emulsion circulating in a line, and to a device for implementing this method. The invention is particularly well-suited for taking a sample of a petroleum effluent in form of an emulsion at wellheads.

During extraction of oil from underground layers, the hydrocarbons recovered at the surface are mixed with salt water. As a result of mechanical pumping, of the reservoir pressure and of the turbulent flow of the fluid in the tubes, the petroleum effluent recovered at the well outlet comes in form of an emulsion. The hydrocarbons can be dispersed in form of drops in water. Generally speaking, in the present document, what is referred to as an emulsion is a liquid consisting of at least two substances, one being dispersed in the other in form of more or less fine drops. The emulsion is characterized, among other things, by the size and the dispersion of the drops in the continuous medium.

In the petroleum sphere, observation of the emulsion formed by the effluent is very important notably to determine the parameters of the separation carried out downstream, the nature and the amounts of demulsifying products possibly used.

However, it is difficult to observe an emulsion because it is unstable by nature. The emulsion formed upon mixing of two substances of different nature does not correspond to a state of equilibrium As soon as the emulsion is left to rest, the drops tend to coalesce. The drops congregate to progressively form increasingly large drops that become less and less numerous, and the two substances eventually come in form of two distinct phases.

The object of the present invention is to take a sample of an emulsion circulating in a line and to stabilize the emulsion sample taken according to a well-known method. Since the size and the distribution of the drops no longer evolve with time, the sample can be observed and analysed after sampling. The invention applies in particular to the field of petroleum industry and it is notably intended to take a sample of a petroleum effluent in form of an emulsion at wellheads.

BACKGROUND OF THE INVENTION

Patent FR-2,590,185-A1 proposes a process for stabilizing an emulsion. The principle consists in coating, in encapsulating the drops in a polymer film impervious to the two substances forming the emulsion, the polymer film being obtained by a polymerization reaction of the outer surface of the drops. This process is applied to water-hydrocarbon emulsions. The polymerization reaction involves a first polymerizing reagent consisting of a lipophilic monomer and a second, hydrophilic polymerizing reagent, both introduced after taking a sample of the emulsion. For further information concerning the drop encapsulation process, the reader can refer to the description of said patent.

The aforementioned patent also describes an application of its stabilization process to collection of an emulsion sample on a permanent-flow circuit, and a device for implementing these processes.

However, the emulsion stabilization process and implementation device presented in the prior art do not allow to stabilize an emulsion as it is in the flowline. In fact, according to the process and to the device of patent FR-2,590,185, the emulsion is altered upon sampling, then after encapsulation upon handling of the emulsion. The way the emulsion sample is taken from the line generates mechanical stresses and movements of the liquid which modify the size and the distribution of the drops. Then, handling of the emulsion after encapsulation leads to deteriorating the polymer film that surrounds the drops, which then tend to restart the coalescence phenomenon.

SUMMARY OF THE INVENTION

The present invention is intended to overcome the drawbacks of the prior art by taking account of the unstable and fragile nature of the emulsion. The idea is to capture a sample as it is in the flowline. Then, while maintaining the sample under pressure and at the temperature prevailing in the line, the drops contained in the emulsion are encapsulated. Finally, the sample is collected without imposing any mechanical stresses thereon.

Generally speaking, in the present description, the <<mechanical stresses>> applied to the emulsion designate any stress that modifies the emulsion when taking a sample thereof or that alters the sample during handling. The <<mechanical stresses>> notably comprise fluid shear, velocity or pressure change of the circulating fluid as a result of section changes in the line, pressure changes of the sample taken. According to the sampling method and to the device of the invention, the mechanical stresses applied to the emulsion during sampling are limited and the mechanical stresses applied to the sample during operations carried out after sampling are minimized.

One had to face two antagonistic phenomena: the instability of the emulsion and sampling of the emulsion necessary for the encapsulation operation. On the one hand, taking a sample leads to suppressing the conditions that have led to the formation and to the maintenance of the emulsion and, on the other hand, to applying mechanical stresses to the emulsion, which may modify the characteristics thereof Furthermore, it is well-known that the pressure influences the structure of the emulsion. A decrease in the pressure applied to the emulsion can lead to an increase in the size of the drops. This shows how important it is to be able to encapsulate the drops while maintaining the sample at the pressure prevailing in the emulsion flow line. After encapsulation, decompression of the sample can no longer change the size of the drops since they are already fixed in a polymer film.

Besides, during encapsulation, one takes care to maintain the temperature of the sample so as to remain close to the emulsion formation conditions.

The process for taking a sample, with a view to analysis, of an emulsion circulating in a main line (1) according to the invention comprises the following stages:
a) placing on said main line (1) a bypass line (2) and distribution means (5a), (5b), (7) and (8) for feeding said emulsion into one or the other of said lines,
b) placing along said bypass line (2) a sleeve (6) provided with a valve (12), (13) at each end,
c) feeding the emulsion into said bypass line (2),
d) taking a sample under pressure by closing valves (12) and (13) arranged at the ends of sleeve (6),
e) injecting encapsulation products so as to stabilize the emulsion sample contained in said sleeve (6), and
f) collecting the stabilized sample in a vessel without applying mechanical stresses thereto.

According to the process of the invention, sleeve (6) can be disconnected from bypass line (2) prior to carrying out stage e).

According to the process of the invention, it is possible to wait for the emulsion to circulate in bypass line (2) prior to carrying out stage d).

According to the process of the invention, the stabilized sample confined in sleeve (6) can be depressurized prior to carrying out stage f).

According to the process of the invention, the sample confined in sleeve (6) can be depressurized by placing sleeve (6) upright, then by opening a depressurization valve (19) arranged in the upper part of sleeve (6).

According to the process of the invention, the sample can be recovered by opening instantaneously valve (13) arranged in the lower part of sleeve (6).

According to the process of the invention, the drops can be encapsulated by injecting a hydrophilic reagent and a lipophilic reagent under pressure into sleeve (6), while gently stirring the sleeve between each injection, the pressure of the sample being maintained constant during injection of the reagents.

The invention also relates to a device allowing to take a sample under pressure of an emulsion circulating in a main line (1) comprising a bypass line (2) that joins said main line (1), distribution means (5a), (5b), (7) and (8) for feeding the emulsion into said main line (1) or into said bypass line (2), said bypass line (2) comprising a sleeve (6) provided with a valve (12), (13) at each end thereof and with at least one means for injecting a stabilizing product.

According to a particular embodiment of the device according to the invention, sleeve (6) is provided with at least four branch connections (18), a branch connection linked to a manometer (14), a branch connection linked to a hydropneumatic accumulator (15) and two branch connections receiving each an injection syringe (16) and (17). Furthermore, the sleeve is provided with unions (10) and (11) allowing to readily disconnect it from bypass line (2).

According to a particular embodiment of the device according to the invention, a depressurization valve (19) is mounted at one end of said sleeve (6).

The present invention can be used in any configuration where an emulsion circulates continuously and permanently. It is however more particularly well-suited to the constraints of petroleum production and notably for sampling of a petroleum effluent in form of an emulsion at wellheads.

The method and the device according to the invention have the advantage of encapsulating the emulsion as it is in the line before sampling and of not altering the polymer film that covers the drops during handling after sampling.

BRIEF DESCRIPTION OF THE DRAWINGS

Other features and advantages of the present invention will be clear from reading the description hereafter of a non-limitative embodiment illustrated by the accompanying drawings, wherein.

DETAILED DESCRIPTION

Figure 1:
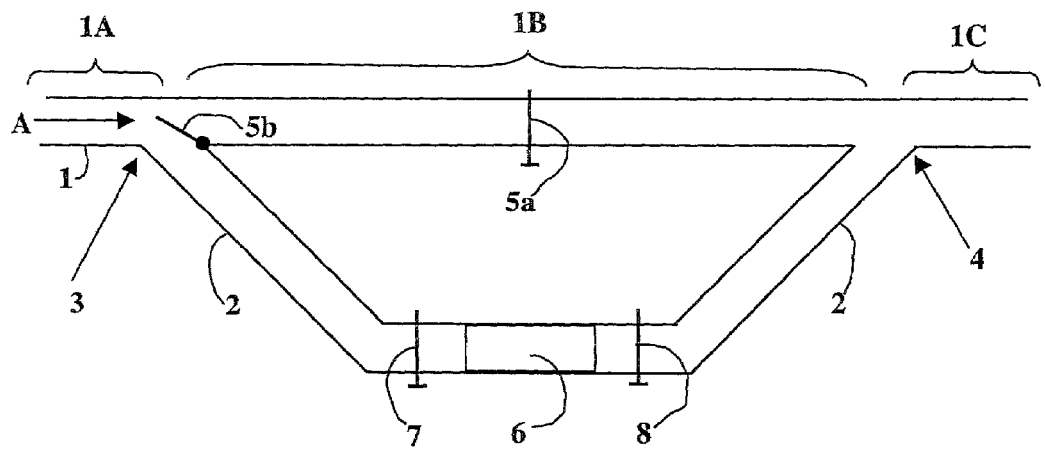
FIG. 1 shows the general architecture of a sampling device.

According to the sampling device shown in FIG. 1, line 2 is a bypass line on main line 1 between junction 3 and junction 4. Main line 1 consists of three parts: 1A, 1B and 1C. According to direction of circulation A of the emulsion, part 1A of the main line is located upstream from junction 3, part 1B is located between junction 3 and junction 4, and part 1C is located downstream from junction 4. Bypass line 2 consists of a sleeve 6 on a line portion. Two valves 7 and 8 surrounding the sleeve are mounted on bypass line 2. Distribution means for feeding the emulsion into main line 1 or bypass line 2 are arranged on the sampling device. According to an embodiment, the distribution means comprise a three-way valve 5a mounted in the vicinity of junction 3 and of valves 7 and 8. According to a second embodiment, the distribution means comprise a valve 5b mounted on main line 1 between junction 3 and 4 and valves 7 and 8.

Actuation of the distribution means (valves 5a, 7 and 8 or valves 5b, 7 and 8) allows to circulate the fluid in direction A from part 1A to part 1C of main line 1 by causing it to flow through either part 1B of main line 1 or through bypass line 2, or simultaneously through part 1B of main line 1 and through bypass line 2.

The layout of bypass line 2 is such that the conditions of flow are the same as in part 1B of main line 1. The flow disturbances caused by bends, section changes, any obstacles or by the distribution means must be similar in bypass line 2 and in part 1B of main line 1. Thus, valves 5a, 5b, 7 and 8 are selected so as not to modify the inner section of bypass line 2.

Figure 2:
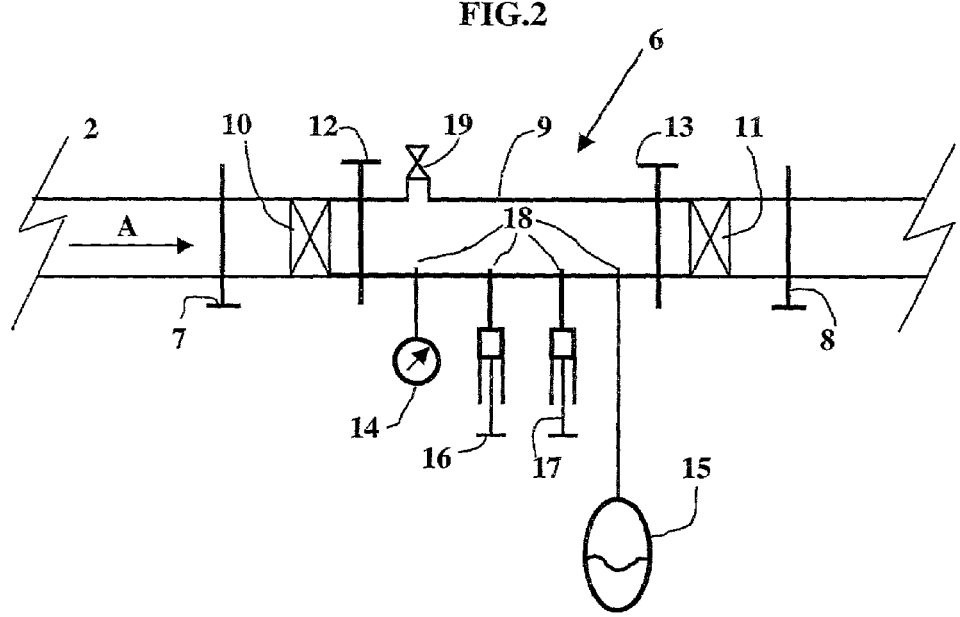
FIG. 2 shows a particular embodiment of the sleeve.

The details of sleeve 6 are shown in FIG. 2. Jacket 9 around retractable sleeve 6 provides thermal insulation. Sleeve 6 is equipped at each end with a quick union and a valve. In direction of circulation A of the emulsion, at the end of the sleeve connected to the part of bypass line 2 coming from junction 3, union 10 is arranged upstream from valve 12. In direction of circulation A of the emulsion, at the end of the sleeve connected to the part of bypass line 2 leading to junction 4, union 11 is arranged upstream from valve 12. The sleeve is provided with at least one injection means 16 or 17 for injecting a stabilization product. More precisely, the injection means consist, on sleeve 6 between valve 12 and valve 13, of two branch connections 18 receiving two injection syringes 16 and 17. Furthermore, sleeve 6 is provided with two other branch connections 18 receiving a manometer 14 and a hydropneumatic accumulator 15.

Syringes 16 and 17 contain the polymerizing reagents intended to be injected under pressure into sleeve 6. Hydropneumatic accumulator 15 allows the internal pressure of the sleeve to be maintained constant by compensating for the pressure variations caused by injection of the polymerizing reagents or by cooling of the sample. Manometer 14 allows to check the constancy of the internal pressure prevailing in the sleeve.

Sleeve 6 exhibits a continuity in the inner section thereof in relation to bypass line 2. Valves 12 and 13, as well as unions 10 and 11 are selected so as not to introduce any obstacle upon passage of the emulsion through sleeve 6. Furthermore, it must be possible to ensure opening and closing of valves 5a (or of valve 5b in the second embodiment), 12 and 13 instantaneously and dependently. Thus, the fluid present in the sleeve can be confined as it is when it flows through bypass line 2 and the sample confined in sleeve 6 can be released without being subjected to shear stresses. Besides, sleeve 6 is provided with a depressurization valve 19 arranged close to valve 12, which allows to depressurize the sample confined under pressure.

In order to improve diffusion of the polymerizing reagents in the sample confined under pressure in sleeve 6, a mixing object (ball or bar) freely moving in sleeve 6 can be introduced.

In order to stabilize an emulsion by means of the device described in connection with FIGS. 1 and 2, the following procedure is carried out: three-way valve 5a is commutated and valves 7 and 8 are closed (or valve 5b is opened and valves 7 and 8 are closed according to the second embodiment) so that the emulsion circulates in direction A, from part 1A to part 1C through part 1B of main line 1, sleeve 6 is connected to bypass line 2 by means of quick unions 10 and 11, valves 12 and 13 of sleeve 6 being open, three-way valve 5a is commutated and valves 7 and 8 are opened (or valve 5b is closed and valves 7 and 8 are opened according to the second embodiment) so that the emulsion flows in direction A from part 1A to part 1C of main line 1 through bypass line 2, one waits for about 10 minutes for the flow to reach equilibrium conditions and notably for bypass line 2 and sleeve 6 to be at the same temperature as the emulsion, simultaneously, valves 12 and 13 are closed so as to confine the emulsion present in the sleeve under pressure and three-way valve 5a is commutated (or valve 5b is opened according to the second embodiment) so that the fluid flows in direction A from part 1A to part 1C through part 1B of main line 1, valves 7 and 8 are closed and the sleeve is disconnected from bypass line 2 by means of quick unions 10 and 11, the hydrophilic reagent present in syringe 16 is injected under pressure into sleeve 6, sleeve 6 is swung ten times so that the hydrophilic reagent diffuses throughout the sample, the lipophilic reagent contained in syringe 17 is injected under pressure into sleeve 6, sleeve 6 is swung ten times so that the lipophilic reagent diffuses throughout the sample, sleeve 6 is arranged upright, with valve 12 in the upper part, depressurization valve 19 is opened so as to progressively bring the sample to the atmospheric pressure, valve 12 is opened, then valve 13 is opened all at once so as not to create fluid shear, the emulsion being collected in a vessel placed below the sleeve.

The sample thus collected is thereafter studied in the laboratory in order to determine the characterization of said emulsion.

What is claimed is:

1. A process for taking a sample, with a view to analysis, of an emulsion circulating in a main line, comprising the following stages:
    a) placing on said main line a bypass line and distribution means, for feeding said emulsion into one or the other of said lines,
    b) placing along said bypass line a sleeve provided with a valve at each end thereof, said sleeve exhibiting a continuity in its inner section in relation to said bypass line,
    c) feeding the emulsion into said bypass line,
    d) taking a sample under pressure by closing said valves arranged at the ends of said sleeve,
    e) disconnecting said sleeve from said bypass line and then injecting encapsulation products to stabilize the emulsion sample contained in said sleeve, and
    f) collecting the stabilized sample to a vessel without applying mechanical stresses thereto.

2. A process as claimed in claim 1, wherein one waits for the emulsion to flow in said bypass line prior to carrying out stage d).

3. A process as claimed in claim 1, wherein the stabilized sample confined in said sleeve is depressurized prior to carrying out stage f).

4. A process as claimed in claim 3, wherein the sample confined in said sleeve is depressurized by placing said sleeve upright, then by opening a depressurization valve arranged in the upper part of said sleeve.

5. A process as claimed in claim 4, wherein the sample is collected by instantaneously opening the valve arranged in the lower part of said sleeve.

6. A process as claimed in claim 1, wherein the drops are encapsulated by injecting a hydrophilic reagent and a lipophilic reagent under pressure into the sleeve, while gently stirring said sleeve between each injection, the pressure of the sample being maintained constant during injection of the reagents.

7. A device for taking a sample under pressure of an emulsion circulating in a main line, comprising a bypass line that joins said main line, distribution means for feeding the emulsion into said main line or said bypass line, said bypass line comprising a sleeve provided with a valve at each end thereof and with at least one injection means for injecting a stabilization product, said sleeve exhibiting a continuity in its inner section in relation to said bypass line and the sleeve being provided with unions for readily disconnecting it from said bypass line.

8. A device as claimed in claim 7, wherein said sleeve is provided with at least four branch connections, a branch connection linked to a manometer, a branch connection lined to a hydropneumatic accumulator, and two branch connections receiving each an injection syringe.

9. A device as claimed in claim 7, wherein a depressurization valve is mounted at one end of said sleeve.

* * * * *